(12) United States Patent
Mekideche

(10) Patent No.: US 8,017,128 B2
(45) Date of Patent: Sep. 13, 2011

(54) COSMETIC ACTIVE INGREDIENT COMPOSED OF ARGININE FERRULATE AND A MICROALGAE EXTRACT AND ITS USES

(76) Inventor: Nicole Mekideche, Ploubazlanec (FR)

( * ) Notice: Subject to any disclaimer, the term of this patent is extended or adjusted under 35 U.S.C. 154(b) by 0 days.

(21) Appl. No.: 12/293,308

(22) PCT Filed: Mar. 27, 2007

(86) PCT No.: PCT/FR2007/000527
§ 371 (c)(1),
(2), (4) Date: Jan. 5, 2009

(87) PCT Pub. No.: WO2007/110511
PCT Pub. Date: Oct. 4, 2007

(65) Prior Publication Data
US 2009/0130139 A1 May 21, 2009

(30) Foreign Application Priority Data
Mar. 27, 2006 (FR) ...................... 06 02628

(51) Int. Cl.
*A61K 36/02* (2006.01)
(52) U.S. Cl. .................... 424/195.17; 562/560
(58) Field of Classification Search ........................ None
See application file for complete search history.

(56) References Cited

U.S. PATENT DOCUMENTS 5,431,912 A * 7/1995 N'Guyen ...................... 424/401
5,824,326 A * 10/1998 Crotty et al. .................. 424/401
2003/0228269 A1 * 12/2003 DeRosa et al. ............... 424/70.1
2004/0116386 A1 * 6/2004 Pifferi et al. .................... 514/78

FOREIGN PATENT DOCUMENTS

EP 0629397 12/1994
FR 2822701 10/2002
JP 07-145067 A * 6/1995

OTHER PUBLICATIONS

Didier C, Kerblat I, Drouet C, Favier A, Béani JC, Richard MJ "Induction of thioredoxin . . . " Free Radic Biol Med. Sep. 1, 2001;31(5):585-98.
Didier C, Pouget JP, Cadet J, Favier A, Béani JC, Richard MJ. "Modulation of exogenous . . . " Free Radic Biol Med. Mar. 1, 2001;30(5):537-46.
Petropoulos I, Conconi M, Wang X, Hoenel B, Brégégère F, Milner Y, Friguet B. "Increase of . . . " J Gerontol A Biol Sci Med Sci. May 2000;55(5):B220-7.
Lee CK, Kiopp RG, Weindruch R, Prolla TA "Gene expression profile of aging and its retardation by caloric restriction" Science. Aug. 27, 1999;285(5432):1390-3.
Ly DH, Lockhart DJ, Lerner RA, Schultz PG "Mitotic misregulation and human aging" Science. Mar. 31, 2000;287(5462):2486-92.
Chondrogianni N, Petropoulos I, Franceschi C, Friguet B, Gonos ES "Fibroblast cultures from healthy centenarians have an active proteasome" Exp Gerontol. Sep. 2000;35(6-7):721.

* cited by examiner

*Primary Examiner* — Susan Hoffman
(74) *Attorney, Agent, or Firm* — Juan J. Lizarraga

(57) ABSTRACT

The invention relates to a novel cosmetic active ingredient composed of a microalgae extract and arginine ferulate, its uses for activating proteasome and the production of thioredoxin, a cosmetic composition containing it and the use of such a cosmetic composition for combating skin ageing.

9 Claims, 4 Drawing Sheets

Figure 1:
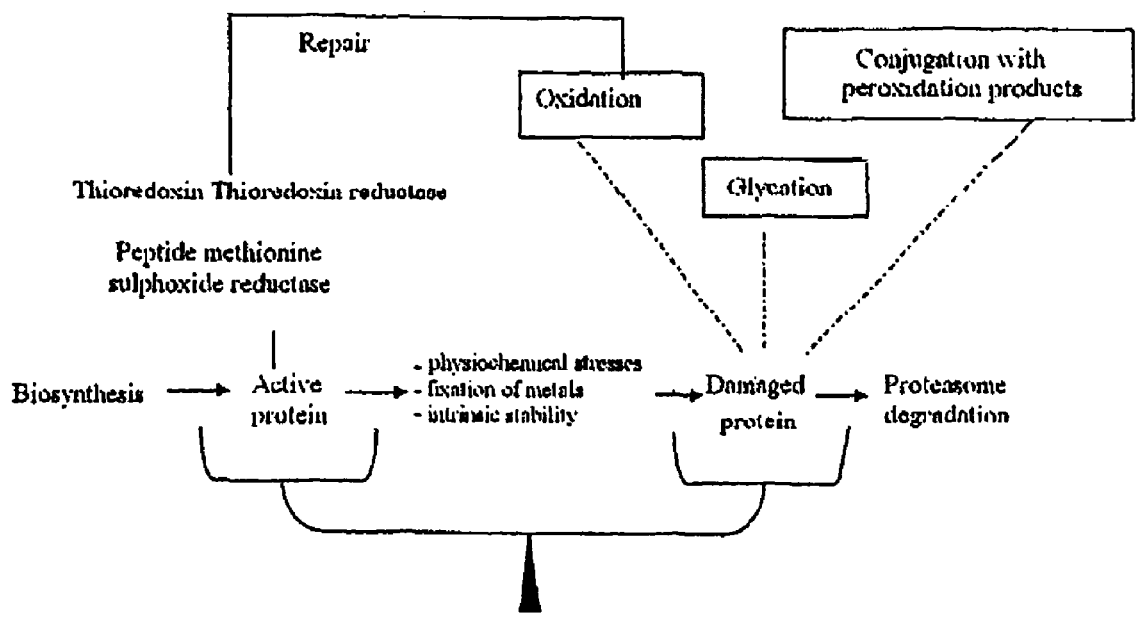

COSMETIC ACTIVE INGREDIENT COMPOSED OF ARGININE FERRULATE AND A MICROALGAE EXTRACT AND ITS USES

The invention relates to an original cosmetic active ingredient composed of a microalgae extract and arginine ferulate, its uses for activating the proteasome and for the production of thioredoxin, a cosmetic composition containing it and the use of such a cosmetic composition for combating skin ageing.

The progressive and irreversible decline of the different physiological functions of the organism, known as ageing, is a complex process controlled by various genetic factors, but also linked to the influences of the outside environment.

Clinically, the signs of ageing are reflected by the appearance of wrinkles and fine lines, by slackening of the cutaneous and subcutaneous tissues, by a loss of skin elasticity, by atony of the skin texture and by yellowing of the skin, which becomes duller and loses its radiance.

Some of these signs are more particularly associated with intrinsic or physiological ageing, i.e. with ageing related to the passing of time, whereas others are more specific for extrinsic ageing, i.e. ageing caused in general by the environment (various forms of pollution: exhaust gases, cigarette smoke, factory fumes, chemical products etc.); this more particularly concerns light-induced ageing which results from exposure to sunlight, to light or to any other radiation.

The changes in the skin resulting from intrinsic or physiological ageing are the consequence of a genetically programmed senescence involving endogenous factors. Over the years, the skin loses elasticity as the dermis produces fewer and fewer collagen and elastin fibres. Hence the progressive weakening of the connective tissue and the slackening of the skin. The ability of the epidermis to renew itself also tends to diminish, the latter becomes drier and thinner as its metabolism is altered. One of the endogenous ageing factors is the reduction in hormone production which leads to the progressive reduction in tissue, cell and organic functions. Hormones such as growth hormone (HGH), testosterone, DHEA and melatonin are produced in large quantities up to the age of 20 years and they promote cell renewal.

By contrast, extrinsic ageing leads to histopathological changes such as an excessive accumulation of elastic material in the upper dermis and degeneration of the collagen fibres.

One of the mechanisms of ageing is the overproduction of free radicals which target the different cell components: proteins, lipids, sugars and DNA. Certain outside influences cause them to start reacting as they are constantly seeking other molecules with which they can combine. They then attack the collagen fibres, the cell membranes and the fatty layer of the skin. They alter the genetic inheritance of the cells, such that the quality of the new skin cells is reduced.

The body protects itself against these attacks by enzyme systems opposing these oxidation reactions (antioxidants). But from the age of twenty, the natural defence mechanisms progressively weaken, such that the skin can no longer defend itself unaided.

The accumulation of damaged proteins constitutes one of the characteristics of cell ageing.

The accumulation of damaged proteins with age therefore poses the problem of the effectiveness of proteolytic systems responsible for the elimination of these proteins and particularly that of the proteasomal system, involved not only in the elimination of the altered, in particular oxidized proteins, but also in the continuous renewal of the intracellular proteins.

In 1956, Harman, in "Free radical theory of aging", proposed that the damage to the different cell components, caused by reactive oxygen species, represents an important factor in the ageing process. Cell ageing would therefore depend on the production of reactive oxygen species, antioxidant defences and the effectiveness of the systems responsible for the elimination of the damaged cell components.

The damaged proteins can be either repaired, or degraded, according to the nature of the alteration. (cf. FIG. 1)

The only known repair mechanisms are the thioredoxin (T)-thioredoxin reductase (TR) system which is capable of reducing the disulphide bridges and the peptide methionine sulphoxide reductase making it possible to reduce the methionine sulphoxide (oxidation product of methionine).

It has been shown in the past that thioredoxin protects against UVB-induced skin damage.

Under normal conditions, the TR reduces oxidized thioredoxin in the presence of NAPDH. The reduced thioredoxin serves as an electron donor to the thioredoxin peroxidase which, as a consequence, reduces $H_2O_2$ to $H_2O$. The TR is a powerful antioxidant against free-radical damage.

The presence of TR integrated in the membrane and in the cytosol has been demonstrated in the human skin.

It has been shown, in UVA-irradiated human skin fibroblasts, that thioredoxin prevents the loss of the mitochondrials membrane potential, the depletion of the cellular ATP content and the loss of cell viability due to irradiation (Didier et al., Free Radical Biology and Medicine, Vol. 31, No. 5, p 585-598, 2001).

It has also been shown that under the oxidative stress conditions caused by UVA, thioredoxin prevents damage to DNA induced by UVA (Didier et al., Free Radical Biology and Medicine, Vol. 30, No. 5, p 537-546, 2001). Thioredoxin is therefore also important for maintaining the integrity of the genome.

The elimination of other types of damage is carried out by the route of proteasome-dependent protein intracellular degradation.

The proteasomal system is constituted by a catalytic complex, the 20S proteasome, and several regulatory components which influence its activity and its specificity. The proteasome is located in mammal cells both in the cytosol and the nucleus. The 20S proteasome is composed of 14 different subunits encoded by genes either of type α, or of type β, and arranged in a cylindrical stack of 4 rings of 7 subunits. Different proteasomal subunits exist (20S, 19S, 26S and PA28, for example) which operate alone or in combination with each other according to the cell metabolism. In fact, they can be either proteasome subunits, or proteasomes as such, the nature of which depends on the cell metabolism.

This proteolytic complex, known as a proteasome, preferentially cleaves the proteins at the level of the carboxy-terminal end of the basic, hydrophobic and acid residues. These peptidase activities are carried by 3 different β subunits and are located inside the structure.

The combination of the 19S regulator with the 20S proteasome forms the 26S proteasome which ensures the degradation of the ubiquitinylated proteins.

With age, an accumulation of damaged proteins takes place, a phenomenon which seems to promote a possible reduction in the effectiveness of the proteasomal system.

In particular, there has been shown on the one hand an age-related increase in the carbonyl content of the proteins in epidermis biopsies as well as in the keratinocytes in culture and on the other hand a modification by adducts derived from carbohydrates and lipids of proteins carrying carbonyl groups. The increase in the quantity of oxidized proteins with age was accompanied by a reduction in the proteasome activity due to the reduction in the quantity of proteasome (Petropoulos et al., J. Gerontol A Biol Sci 2000; 55A:B220-7).

Two recent studies, one on the post-mitotic ageing of skeletal muscle cells of rats and the other on human fibroblasts, where the expression of 6000 genes was studied by microarrays, have shown a variation in expression of less than 1% of the genes during cell ageing, including the genes of the proteasomal system the expression of which was reduced. (Lee et al., Science 1999; 285: 1390-3 and Lee et al., Science 2000; 287:2486-92).

A reduction has also been shown in the expression of the transcripts for the 3 proteasome subunits (X, N3 and C2) analyzed in cells of elderly donors, whereas cultured cells of four centenarians retain a level of expression and proteasome activity close to that of young donors. (Chondrogianni et al., Exp Gerontol 2000; 35.721-8).

All of these results clearly indicate that there is a reduction in proteasome activity with age.

Another category of "modified" proteins is also involved in the ageing mechanism. These are so-called "glycated" proteins. Glycation is a post-translational modification of proteins initiated by the condensation of reducing sugars with "amino" type groups via the Maillard reaction. The products obtained are commonly referred to as being advanced glycation end products (AGEs). The two main glycation products, carboxymethyl lysine (CML) and pentosidine, accumulate during ageing and in an accelerated manner in pathologies such as diabetes.

The toxicity of the glycated products is known. There may be mentioned as examples their harmful effects, such as the alteration of enzymatic activities, the cross-linking of proteins and the formation of aggregates, the alteration of the endothelium-basal membrane interface, the reduction in the susceptibility to proteolysis, the failure to recognize molecular signals and endocytosis, and the modification of immunogenicity.

The glycation of proteins promotes their oxidizability, the glycated proteins being able to react with oxygen to form oxygenated free radicals the harmful effects of which have been indicated previously.

These glycated proteins cannot be destroyed or released from the cell in which they accumulate and prove resistant to degradation by the proteasome. Glycation has consequences throughout the organism and in particular plays an important role in the genesis of certain diseases by causing cell and tissue lesions, and accelerated ageing of the tissues.

Consequently there is a need to develop active ingredients for avoiding glycation of the proteins and their accumulation in the cell system.

Generally, it is of particularly great interest to have access to preparations for topical use which would make it possible to delay cutaneous ageing, in particular by improving the proteasome activity and by reducing the number of glycated proteins.

Patent Application FR 2 822 701 describes the use of an extract of the alga *Phaeodactylum* (microalga) as a cosmetic agent promoting proteasome activity and for the manufacture of a cosmetic composition protecting the skin against the adverse effects of UV exposure or for preventing and/or delaying skin ageing effects.

Patent Application EP 0 629 397 A1 describes an anti-free radical and anti-inflammatory cosmetic composition comprising a hydroglycolic extract of *Chlorella, Scenedesmus* and *Spiruline* algae (ARL) and an extract of green coffee.

Given the above, the Applicant has developed an active ingredient resulting from a synergetic combination of compounds corresponding to a triple objective.

The first objective corresponds to the need to improve the proteasome activity in order to promote the elimination of proteins dependent on the latter. The second corresponds to that of stimulating the production of thioredoxin in synergetic manner. Finally, the third objective corresponds to the requirement to substantially reduce the production of glycated proteins and, as a result, their accumulation in the cells.

The Applicant has surprisingly discovered a novel cosmetic active ingredient composed of arginine ferulate and an extract of microalga, which activates the proteasome and the production of thioredoxin, whilst avoiding the glycation of the proteins.

Novel cosmetic preparations for topical use comprising this active ingredient also form part of the invention and can be used to slow down cutaneous ageing.

The main object of the present invention is a cosmetic active ingredient composed of arginine ferulate and an extract of microalga.

By "microalga" is meant an undifferentiated unicellular or pluricellular microscopic alga, as opposed to a "macroalga" the life cycle of which comprises differentiated stages.

By "extract of microalga", is meant any cell extract originating from a microalga and capable of being used in the cosmetic active ingredient of the invention. Such an extract can be, for example, an intracellular, membrane or lipid extract.

The microalga strain is cultured in a standard culture medium containing trace elements, such as, for example, manganese, copper, silicon, boron, sulphur, hydrolyzed proteins, all at a pH comprised between 7 and 8 and at a temperature promoting its growth, usually comprised between 25 and 30° C. When the growth is optimum, i.e. when the number of cells will no longer grow in the culture medium, the culture medium is recovered and centrifuged. If appropriate, this centrifuged culture is then subjected to an oxidative stress by the addition of 1 to 5 ml of hydrogen peroxide per litre of medium ($H_2O_2$) or by ozone, which is generated using an ozone generator by reaction of the air with UV. The biomass thus obtained is then centrifuged once again and the pellet is recovered.

Arginine ferulate is a synthetic molecule derived from arginine. Its production method is described in detail in Example 1.

The Applicant has therefore surprisingly found that it is possible with such a combination of compounds to improve the proteasome activity in order to promote the elimination of proteins dependent on the latter, while stimulating the production of thioredoxin in a synergetic manner. This improvement is much better than with the extract of microalga alone.

Moreover, the cosmetic active ingredient of the invention makes it possible to substantially reduce the production of glycated proteins and, as a result, their accumulation in the cells. Moreover, the reduction in the glycated proteins also gives rise to an improvement in the proteasome activity leading to a significantly greater elimination of the damaged proteins.

The Applicant has observed that it is possible to obtain a 50% reduction in glycated proteins by treating cells with 0.005%-0.02% arginine ferulate. This represents the content required to inhibit 50% of the formation of glycated proteins in the cells.

It appears, in fact, that the active ingredient has the particular advantage of combining the extract of alga and arginine ferulate which, when it is brought into contact with the skin, disintegrates into arginine and ferulic acid due to the skin's enzymatic systems.

L-arginine, a basic amino acid, has a regenerative effect on the skin cells by avoiding the glycation of proteins but still has the drawback of being unstable on contact with the oxygen in the air for example, and it degrades to cytotoxic products. Ferulic acid, however, is an antioxidant agent capable of absorbing UV rays. The Applicant has therefore shown that the arginine ferulate complex (or ferulic acid/arginine complex) increases the stability of the arginine formed and therefore improves the activity of this arginine. Such an arginine ferulate complex therefore leads in particular to an increased bioavailability of arginine in tissue, in particular when applied directly to the skin.

The improvement in the proteasome activity by the active ingredient of the invention, relative to that obtained with the extract of microalga alone, is observed by the reduction in the level of non-hydrolyzed oxidized proteins present in cells, such as human or animal skin cells, for example of keratinocyte, fibroblast or melanocyte type. This reduction is typically located within the range of values comprised between 10 and 25%.

Moreover, the presence of arginine ferulate, in combination with the extract of microalga, preferably enriched with phytoalexins (see below), leads to increased production of thioredoxin in the cells, with respect to the extract of microalga alone.

Thus, as an example, the use of increasing quantities of arginine ferulate comprised between 0.005% and 0.1% by weight of the product in which it is contained, preferably between 0.005% and 0.05%, in particular between 0.005% and 0.02%, the extract of microalga being comprised between 0.995% to 0.90%, preferably between 0.995% and 0.95%, in particular between 0.995% and 0.98%, has made it possible to show that an increase of approximately 4-20%, preferably 4-10%, in particular 4-8%, in the production of thioredoxin can be obtained relative to the extract of microalga alone contained in the same product according to the abovementioned values by weight. This constitutes a decisive advantage of the invention. For example, by "product in which it is contained" is meant a cosmetic composition as defined hereafter.

In a particular embodiment of the invention the extract of microalga of the active ingredient according to the invention is enriched with phytoalexins, for example by placing the microalgae in a situation of stress, preferably a situation of oxidative stress due to $H_2O_2$ or ozone, as indicated above.

Phytoalexins are so-called "defence" compounds which are synthesized by plants and, in particular by microalgae, when the latter are placed under stress conditions and, preferably, under oxidative stress conditions. These phytoalexins can be different in nature: antibiotic, enzymatic, phenolic. In the present case, an enzymatic system is involved, such as for example, ferredoxin-NADP+ oxydoreductase (FNR), superoxide dismutase (SOD) and glutathione peroxidases.

In a preferred embodiment of the invention the extract of microalga of the active ingredient according to the invention originates from a microalga of the class of the Chlorophyceae. These are green algae found in lakes and ponds which contain a high chlorophyll content. In a particularly preferred manner, the microalga used belongs to the genus *Scenedesmus* which is a fresh water alga and to the genus *tetracystis*.

The active ingredient according to the invention preferably has an arginine ferulate: extract of microalgae ratio by weight comprised between 1:1 and 1:199, preferably between 1:19 and 1:99, quite preferably 1:30 and 1:50 and particularly preferably 1:19.

Another object of the invention relates to the in vitro or ex-vivo use of an active ingredient according to the invention for activating the proteasome of cells, such as human or animal skin cells, for example of keratinocyte, fibroblast or melanocyte type. This activation is reflected by increased degradation of the oxidized proteins in the presence of the active ingredient according to the invention.

An additional object of the invention relates to the in vitro or ex-vivo use of an active ingredient according to the invention for stimulating the production of thioredoxin.

Another object of the present invention relates to the use of an active ingredient according to the invention for the manufacture of a cosmetic composition for topical use.

Advantageously, the active ingredient is present in quantities comprised between 0.1% and 2%, preferably between 0.5% and 2%, in particular between 1% and 2% by weight with respect to the total weight of the cosmetic composition.

By way of example, such cosmetic compositions for topical use are solutions or dispersions of lotion type, oil in water (O/W) or water in oil (W/O) emulsions, creams and gels. They can be more specifically compositions or lotions for the protection of the face, body and hands, day creams, sun creams, cleansing milks, anti-wrinkle creams and bath compositions. Apart from the active ingredient of the invention, all these compositions advantageously contain standard active ingredients and conventional excipients used in cosmetic compositions intended for the skin. There may be mentioned tocopherol linoleate, emollients, perfumes, preservatives, colorants, emulsifying agents, texturizing agents and, if appropriate, sun filters.

An additional object of the present invention relates to a cosmetic composition for topical use comprising the active ingredient according to the invention in a physiologically acceptable medium, this cosmetic composition being able to correspond, for example, to a cream, lotion, gel and mask or to others mentioned above, and the use of such a composition for combating skin ageing.

An example of a cosmetic composition contains 1% of cosmetic active ingredient of the invention, 2% glycerine, 0.80% Carbomer, 2.00% sorbitan stearate, 2.00% polysorbate 60, 8.00% octyldodecanol, 0.80% Trisamino® and the remainder being demineralized water. The percentages are expressed by weight relative to the total weight of the composition.

The following examples illustrate the invention without limiting its scope.

EXAMPLE 1

Arginine Ferulate Production Method

Arginine ferulate is produced by mixing arginine ($HN=C(NH_2)-NH-(CH_2)_3-CH(NH_2)-COOH$) and ferulic acid (=3-methoxy 4-hydroxycinnamic acid).

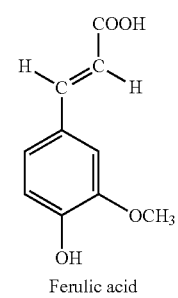

Ferulic acid

The thorough mixing of the two powders takes place in a powder mixer (Lödige) at 20 rpm for approximately 48 hours.

EXAMPLE 2

Cell Culture

Primocultures of keratinocytes are obtained from a human skin biopsy followed by enzymatic digestion of the cell membranes in order to preserve the intracellular medium in a KGM culture medium (complete culture medium, without serum, the final calcium concentration of which is 0.05 mM) supplemented with EGF ("Epidermal Growth Factor").

The cells were studied after different passages (P2, P4, P6 and P8) and after UVB irradiation with the aim of evaluating the influence of the active ingredient of the invention on senescent cells. Within the framework of the invention, the term "passage" has the standard meaning in the field of cell cultures. The passage P1 represents the time necessary for the primoculture cells to reach confluency. After this, a subculture of the culture medium P1 is carried out, which is cultured, in the medium defined above, for the time necessary to reach confluency defining passage P2, and so on, which makes it possible to define the passages P4, P6 and P8.

The tests were carried out with keratinocytes from a 15 year-old donor serving as a reference for an optimum proteasomal activity, and those from a 62 year-old donor, whose proteasomal system functions less efficiently than that of the 15 year-old donor. The 15 year-old donor's cells were irradiated in order to measure the proteasomal capacity and compare it to that of the 62 year-old donor. In fact, UVB irradiation gives rise to a deterioration in the functioning of the proteasomal system.

These keratinocytes are cultured in the KGM medium supplemented with EGF, defined above, in the presence of the active ingredient, denoted "product B", comprising:
- 99.5% of an extract of microalga of the genus *Scenedesmus* having undergone oxidative stress with $H_2O_2$ or ozone, as indicated above, and
- 0.5% arginine ferulate.

These keratinocytes are also cultured in the presence of the active ingredient comprising only product A which represents a pure extract of microalga of the genus *Scenedesmus* having undergone an abovementioned oxidative stress.

The same experiments are carried out in the absence of product A or B (so-called "control" sample).

Three cultures of keratinocytes were carried out in KGM medium supplemented with EGF:
Normal physiological conditions: cells in culture from a donor aged 15
Physiological cell senescence conditions: cells in culture from a donor aged 62
Photo-induced senescence conditions: cells in culture from a donor aged 15, UVB irradiated at a rate of 100-150 mJ/cm$^2$ of culture medium. The UVB source is obtained by means of a UV lamp (Biosun, Viber Lourmat-France), the irradiation wavelength being approximately 315 nm.

EXAMPLE 3

Cell Viability Measurement

The cells obtained under the conditions of Example 2 are studied at passages P2, P4, P6 and P8. The different passages make it possible to note the cell ageing of the donor as well as the ageing due to the culture conditions after the different cell passages. In fact, after the removal of the cells from the epidermis, a difference in the cell viability is observed from the start of the culture ("control" sample). This difference is accentuated after the different cell passages.

The consequences of cell senescence were studied by measuring the cell viability which was evaluated by the reduction test with blue formazan (MMT). The tetrazolium salt (MTT) has the property of being reduced to blue formazan crystals by the mitochondrial succinate dehydrogenase of the cells. This enzyme, which plays an important role in the Krebs cycle, catalyzes the dehydrogenation of the succinate to fumarate.

The activity of this enzyme, a flavoprotein very strongly attached to the mitochondrial internal membrane, is measured by the reduction of MTT. The absorbance (or optical density) directly linked to the activity of the succinate dehydrogenases, itself linked to cell viability, is measured by spectrophotometric assay at 595 nm by means of a conventional device, such as a spectrophotometer equipped with a data processing computer system. Cell viability increases as the absorbance value rises.

The three culture conditions of Example 2 were studied.

The same experiments were repeated with product A alone, representing a pure extract of microalga of the genus *Scenedesmus* having undergone an oxidative stress defined previously.

Results Under Normal Physiological Conditions (Donor Aged 15)

|  | Control (% V) | P2 (% V) | P4 (% V) | P6 (% V) | P8 (% V) |
|---|---|---|---|---|---|
| Viability without product A (%) | 100 | 97 | 93 | 79 | 69 |
| Viability with 1% product A (%) | 100 | 95 | 94 | 81 | 74 |
| Viability without product B (%) | 100 | 95 | 91 | 79 | 63 |
| Viability with 1% product B (%) | 100 | 95 | 94 | 83 | 75 |

Results Under Physiological Senescence Conditions (Donor Aged 62)

|  | Control (% V) | P2 (% V) | P4 (% V) | P6 (% V) | P8 (% V) |
|---|---|---|---|---|---|
| Viability without product A (%) | 100 | 84 | 66 | 48 | 41 |
| Viability with 1% product A (%) | 100 | 87 | 70 | 51 | 47 |
| Viability without product B (%) | 100 | 88 | 69 | 56 | 51 |

-continued

|  | Control (% V) | P2 (% V) | P4 (% V) | P6 (% V) | P8 (% V) |
|---|---|---|---|---|---|
| Viability with 1% product B (%) | 100 | 93 | 77 | 71 | 61 |

Results Under Photoinduced Senescence Conditions (Donor Aged 15+UVB 100 mJ/cm² of Culture)

|  | Control (% V) | P2 (% V) | P4 (% V) | P6 (% V) | P8 (% V) |
|---|---|---|---|---|---|
| Viability without product A (%) | 100 | 74 | 62 | 48 | 33 |
| Viability with 1% product A (%) | 100 | 81 | 68 | 57 | 45 |
| Viability without product B (%) | 100 | 86 | 78 | 59 | 48 |
| Viability with 1% product B (%) | 100 | 93 | 81 | 66 | 54 |

% V: % Viability,
% product A and B: content of product A or B per 100 g of culture medium.

The results show that during the different passages the cell viability reduces, more rapidly in the case of the donor aged 62 than in the case of the donor aged 15.

Moreover, the reduction in cell viability following UVB irradiation of cells originating from a donor aged 15 is comparable to the physiological reduction in the donor aged 62.

The viability of the cells treated with product B is significantly higher than that of the cells treated with product A, independently of the ageing conditions:
- whether it is a matter of cell ageing taking place during culture (donor aged 15).
- whether it is a matter of cell ageing dependent on the initial state of the cells and continuing during the culture (donor aged 62),
- or it is a matter of photo-induced cell ageing.

EXAMPLE 4

Purification of the Three Proteasome Subunits, 20S, 26S and PA28 Respectively

Within the framework of this example, the 20S, 26S and PA28 proteasomes represent subunits.

Extracts from cells cultured in the medium defined previously according to Example 2, under two physiological conditions, which correspond to normal physiological cells (donor aged 15) and to normal senescent cells (donor aged 62), are centrifuged at 10000 g for 16 hours at 4° C.

The pellet is dissolved in Tris-HCl buffer (25 mM, pH 7.5), then applied to a CNBr Sepharose column (on which is grafted a monoclonal antibody directed against the subunit of the human proteasome to be purified) previously equilibrated with Tris-HCl buffer (25 mM, pH 7.5). The column is then washed with the same buffer then the proteasome subunit is eluted with Tris-HCl containing 2M NaCl (pH 8) and is dialyzed for 16 hours at 4° C. (or applied to a gel filtration column (PD10 Sephadex)).

A sample of the purified proteasome subunit is mixed with denaturing loading buffer (SDS 0.1%) then incubated at 100° C. for 5 minutes. The proteins contained in the eluate are separated by acrylamide gel electrophoresis (SDS-PAGE) at 12%. The migration is carried out at ambient temperature at a constant voltage of 80V for 30 minutes, then 120V for 2 hours.

EXAMPLE 5

Measurement of the Proteasome Activity by Measuring the Activity of the Three Proteasome Subunits (20S, 26S, PA28) Under the Three Culture Conditions of Example 2

The peptidase activities of the proteasome were measured by the use of a substrate formed by synthetic peptides the N-terminal ends of which are blocked and the C-terminal ends of which are linked by an isopeptide bond to a fluorescent radical: 7-amido-4-methyl-coumarin (MCA) These non-fluorescent radicals when they are linked to the peptides, become fluorescent in the free state after proteolytic cleavage. The mixture, containing either 50 µg of crude homogenate of total proteins, representing the pellet of Example 4, or 3 µg of purified proteasome (in 25 mM Tris-HCl, pH 7.5) is incubated at 37° C. with the peptide substrate in a final volume of 200 µl for 30 min.

The reaction is stopped by the addition of 300 µl of an acid, for example hydrochloric acid, or ethanol. After the addition of 2 ml of distilled water, the fluorescence is measured using a commercially available micro-plate reader, at excitation and emission wavelengths of 350/440 m for the MCA. The proteasome activities are determined as the difference between the total activity, i.e. that measured at the start of the experiment, before the addition of the substrate, and the remaining activity of the crude extract, i.e. after reacting the substrate and after purification.

The activities are expressed in ng of proteasome/min/mg of total proteins present in the cell extract.

Results Under Normal Physiological Conditions (Donor Aged 15, Passage P2)

|  | 20S Proteasome (nmoles/min/m) | 26S Proteasome (nmoles/min/mg) | PA28 Proteasome complex (nmoles/min/mg) |
|---|---|---|---|
| Substrate | 10.5 ± 0.5 | 74.2 ± 2.5 | 345.0 ± 25.2 |
| Substrate + 0.1 % of product B | 9.1 ± 0.4 | 75.8 ± 5.1 | 361.2 ± 21.7 |
| Substrate + 0.5% of product B | 12.0 ± 1.8 | 83.2 ± 7.8 | 362.5 ± 10.2 |
| Substrate + 1% of product B | 11.8 ± 1.2 | 87.2 ± 10.2 | 370.5 ± 24.3 |

Results Under Physiological Senescence Conditions (Donor Aged 62)

|  | 20S Proteasome (nmoles/min/m) | 26S Proteasome (nmoles/min/mg) | PA28 Proteasome complex (nmoles/min/mg) |
|---|---|---|---|
| Substrate | 7.3 ± 0.7 | 52.7 ± 4.0 | 180.2 ± 18.1 |
| Substrate + 0.1% of product B | 8.4 ± 0.3 | 63.0 ± 4.2 | 198.0 ± 10.5 |

-continued

|  | 20S Proteasome (nmoles/min/m) | 26S Proteasome (nmoles/min/mg) | PA28 Proteasome complex (nmoles/min/mg) |
|---|---|---|---|
| Substrate + 0.5% of product B | 9.6 ± 1.4 | 69.4 ± 5.6 | 228.6 ± 13.1 |
| Substrate + 1% of product B | 12.0 ± 1.1 | 76.2 ± 2.3 | 264.2 ± 18.4 |

Results Under Photoinduced Senescence Conditions (Donor Aged 15, UVB 100 mJ/cm$^2$)

|  | 20S Proteasome (nmoles/min/mg) | 26S Proteasome (nmoles/min/mg) | PA28 Proteasome complex (nmoles/min/mg) |
|---|---|---|---|
| Substrate | 6.2 ± 0.4 | 54.8 ± 7.2 | 195.7 ± 21.2 |
| Substrate + 0.1% of product B | 8.5 ± 1.1 | 63.7 ± 2.4 | 227.1 ± 17.4 |
| Substrate + 0.5% of product B | 11.4 ± 1.7 | 70.2 ± 3.5 | 244.3 ± 13.6 |
| Substrate + 1% of product B | 12.1 ± 1.4 | 81.2 ± 8.2 | 269.3 ± 11.8 |

The results show greater activity of the three proteasome subunits under normal physiological conditions relative to physiological and photoinduced senescence conditions.

Treatment of the cells with product B leads to a re-establishment of the activity of the three proteasome subunits under senescence conditions. The activity is restored in order to reach the overall level measured under non-senescent physiological conditions.

Figure 2:
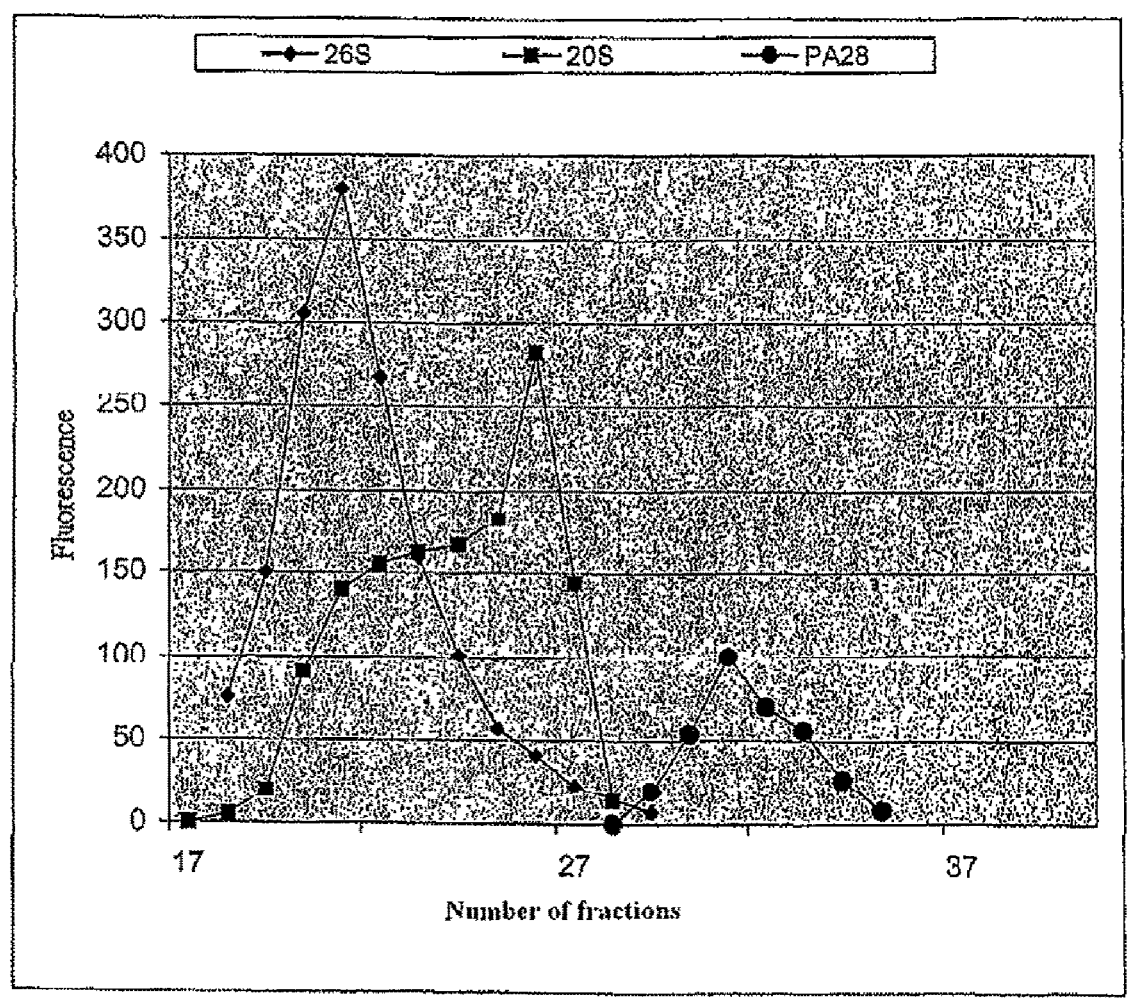
Figure 3:
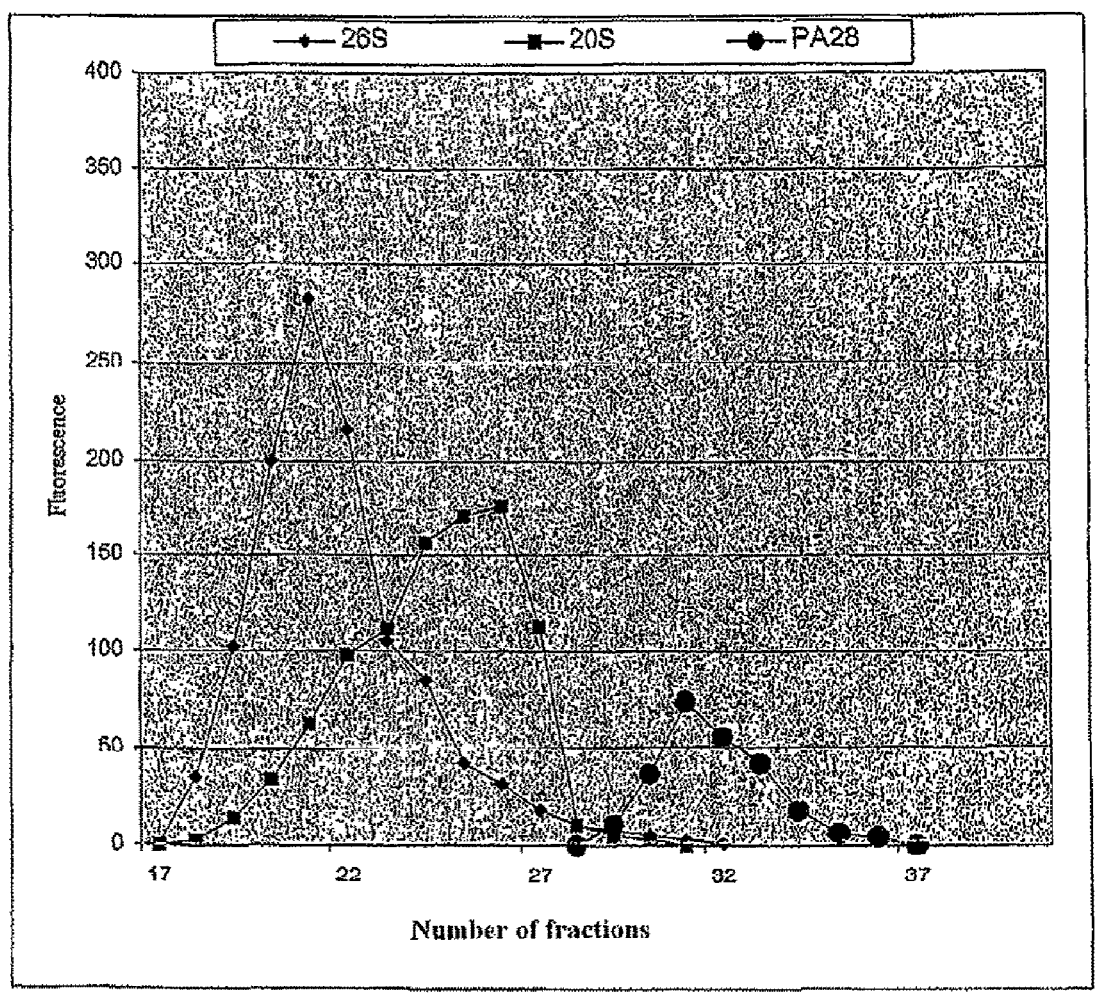
Figure 4:
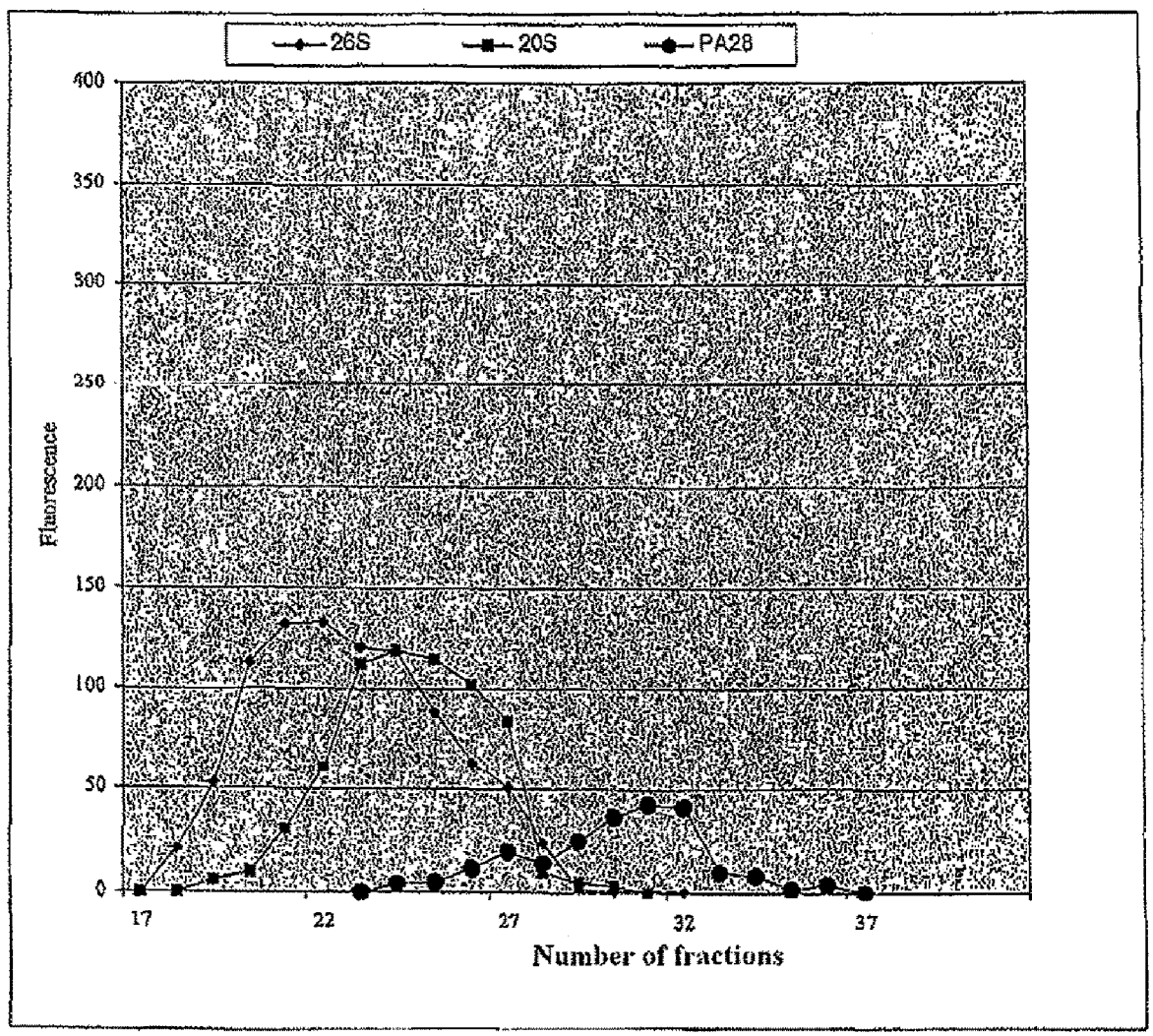

The results are given in particular in FIGS. 2, 3 and 4), which represent:

FIG. 2: donor aged 15
FIG. 3: donor aged 62
FIG. 4: donor aged 15+photoinduced senescence conditions (UVB)

The three figures above represent the fluorescence measurement of a sample as a function of the purification fractions collected.

EXAMPLE 6

Measurement of the Proteasome Activity by Assay of the Quantity of Non-Hydrolyzed Oxidized Proteins Under the Three Culture Conditions of Example 2

The detection of the oxidized proteins was carried out using the Oxyblot® kit (Oxidized Protection Detection Kit, Chemicon International). The cytosolic extracts of keratinocytes, i.e. the intracellular extracts obtained after enzymatic digestion defined according to Example 2, in the presence of product B, are treated for 15 minutes with 2,4-dinitrophenylhydrazine, then are separated by acrylamide gel electrophoresis at 12% (SDS-PAGE) with an amount of 10 μg of proteins deposited per well. The gels are then transferred to a nitrocellulose membrane (Nitrocellulose Hybond). The hydrazones formed are immunodetected using rabbit polyclonal antibodies directed against the 2,4-[alpha]dinitrophenyl radical (Sigma, Ref D-9656). In order to detect the proteins ubiquitinated or modified by the adduct 4-hydroxy-2-nonenal, 20 μg of proteins are deposited on 12% polyacrylamide gel and the corresponding Western blots are developed using polyclonal antibodies directed against ubiquitin. The detection of the antigen-antibody complexes is carried out with secondary rabbit antibodies coupled with the peroxidase.

The same experiments are carried out with product A defined previously.

Results Under Normal Physiological Conditions (Donor Aged 15)

|  | Quantity (unit/mm$^2$) | Quantity In the presence of 1% of product A (unit/mm$^2$) |
|---|---|---|
| Control (P1) | 22 ± 1.1 | 15 ± 2.0 |
| P2 | 26 ± 1.4 | 21 ± 1.4 |
| P4 | 37 ± 2.8 | 29 ± 3.2 |
| P6 | 51 ± 4.1 | 41 ± 4.2 |
| P8 | 64 ± 4.0 | 55 ± 6.0 |
|  |  | Quantity In the presence of 1% of product B (unit/mm$^2$) |
| Control (P1) | 18 ± 2.0 | 12 ± 0.6 |
| P2 | 21 ± 1.5 | 17 ± 1.2 |
| P4 | 31 ± 4.2 | 27 ± 1.7 |
| P6 | 45 ± 3.4 | 36 ± 2.4 |
| P8 | 57 ± 4.0 | 45 ± 3.2 |

Results Under Physiological Senescence Conditions (Donor Aged 62)

|  | Quantity (unit/mm$^2$) | Quantity In the presence of 1% of product A |
|---|---|---|
| Control (P1) | 100 ± 7.6 | 90 ± 10.2 |
| P2 | 131 ± 15.2 | 113 ± 7.8 |
| P4 | 183 ± 13.7 | 151 ± 10.0 |
| P6 | 251 ± 21.1 | 205 ± 13.7 |
| P8 | 375 ± 12.3 | 321 ± 15.2 |
|  |  | Quantity In the presence of 1% of product B (unit/mm$^2$) |
| Control (P1) | 90 ± 10.7 | 79 ± 4.2 |
| P2 | 123 ± 11.2 | 95 ± 10.2 |
| P4 | 170 ± 9.7 | 134 ± 8.4 |
| P6 | 233 ± 14.6 | 187 ± 11.1 |
| P8 | 349 ± 21.2 | 285 ± 13.2 | mm$^2$: mm$^2$ of culture medium

The results show that product B leads to a clear reduction in the quantity of oxidized proteins in both the donor aged 15 and the donor aged 62. The effect is more marked in the case where the experiments are carried out with product B. It is possible to estimate the reduction of the quantity of these proteins at approximately 12%-15% with respect to the case where product A alone is used.

EXAMPLE 7

Measurement of the Thioredoxin Reductase (TrxR) Activity

The TrxR activity in the cell extracts from cells cultured according to Example 2, treated or untreated (control) with product B, is determined by measuring the TrxR concentration by the Biuret method after reaction with thioredoxin (Trx) and by comparison with the known activity of a purified TrxR.

A volume corresponding to 50 µg of proteins of each cell extract is incubated with a mixture of HEPES, 80 mM pH 7.5, 0.9 mg/ml of NADPH, EDTA 6 mM, 2 mg/ml of insulin and 10 µM of Trx of *E. coli*, at 37° C. for 20 minutes in a final volume of 120 µL. The reaction is stopped by the addition of 500 µL of DTNB (dithio-bis-nitrobenzoic acid) (0.4 mg/ml) in guanidine hydrochloride 6 M/Tris-Cl 0.2 M (pH 8.0). A control sample containing everything except the Trx is incubated and treated in the same way as each sample.

The absorbance at 412 nm is measured and the value of the control subtracted from the value of the corresponding absorbance of the sample.

A standard curve is prepared using TrxR from purified calf thymus, with a defined specific activity.

The absorbance values of the samples are compared to the standard curve and the activity is deduced.

The same experiments are carried out with Product A.

The activities are expressed in ng of TrxR/mg of total proteins present in the cell extract.

Results Under Normal Physiological Conditions (Donor Aged 15)

|  | Activity (ng of TrxR/mg of total proteins) | % |
|---|---|---|
| Control | 208.2 ± 5.8 | |
| 0.5% of product A | 218.3 ± 8.2 | +5 |
| 1% of product A | 228.0 ± 10.1 | +10 |
| 2% of product A | 235.4 ± 9.2 | +13 |
| Control | 208.2 ± 5.8 | |
| 0.5% of product B | 220.2 ± 8.3 | +6 |
| 1% of product B | 238.0 ± 10.1 | +14 |
| 2% of product B | 251.0 ± 9.8 | +21 |

Results under Normal Physiological Conditions (Donor Aged 15) in the Presence of Acrolein, a Thioredoxin Reductase Inhibitor

|  | Activity (ng of TrxR/mg of total proteins) | % |
|---|---|---|
| Control | 208.2 ± 5.8 | |
| Acrolein (25 µM) | 130.8 ± 11.4 | −37 |
| Acrolein (25 µM) + 0.5% of product B | 139.0 ± 12.5 | +6 |
| Acrolein (25 µM) + 1% of product B | 149.2 ± 10.1 | +14 |
| Acrolein (25 µM) + 2% of product B | 160.4 ± 13.8 | +23 |
| Control | 208.2 ± 5.8 | |
| Acrolein (25 µM) | 130.8 ± 11.4 | −37 |
| Acrolein (25 µM) + 0.5% of product A | 141.0 ± 15.2 | +8 |
| Acrolein (25 µM) + 1% of product A | 145.6 ± 10.0 | +11 |
| Acrolein (25 µM) + 2% of product A | 155.8 ± 13.8 | +19 |

Acrolein (25 µM): Concentration of acrolein in the culture medium.

Results Under Physiological Senescence Conditions (Donor Aged 62)

|  | Activity (ng of TrxR/mg of total proteins) | % |
|---|---|---|
| Control | 132.0 ± 8.1 | |
| 0.5% of product A | 144.8 ± 10.1 | +9 |
| 1% of product A | 160.6 ± 11.0 | +21 |
| 2% of product A | 170.3 ± 9.7 | +28 |
| Control | 132.0 ± 8.1 | |
| 0.5% of product B | 148.8 ± 10.2 | +13 |
| 1% of product B | 159.4 ± 9.3 | +21 |
| 2% of product B | 176.6 ± 11.0 | +34 |

It is noted that the presence of product B in the cell extracts as defined above increases the activity of thioredoxin reductase (TrxR) relative to a control which does not contain it. Moreover, the activity of the TrxR increases in proportion to the quantity of product B added.

This activity with product B is greater than when such cell extracts are treated with the product A alone.

Results Under Photoinduced Senescence Conditions (Donor Aged 15, UVB 100 mJ/cm² of Culture)

|  | Activity (ng of TrxR/mg of total proteins) | % |
|---|---|---|
| Control | 208.2 ± 5.8 | |
| UVB | 246.3 ± 22.3 | +18 |
| UVB + 0.5% of product A | 241.0 ± 12.0 | +16 |
| UVB + 1% of product A | 259.0 ± 16.2 | +24 |
| UVB + 2% of product A | 270.4 ± 13.7 | +30 |
| Control | 208.2 ± 5.8 | |
| UVB | 246.3 ± 22.3 | +18 |
| UVB + 0.5% of product B | 251.8 ± 11.2 | +21 |
| UVB + 1% of product B | 267.2 ± 9.7 | +28 |
| UVB + 2% of product B | 278.5 ± 11.4 | +34 |

The same conclusions arrived at above apply here.

EXAMPLE 8

Measurement of the Thioredoxin Level

The level of thioredoxin in the cell extracts from cells cultured according to Example 2, treated or untreated (control) with product B or with product A alone is measured by ELISA.

96-well plates are incubated with 100 µl per well of the anti-Trx monoclonal antibody clone 2G11 (5 µg/ml; BD Pharmingen) in carbonate buffer, pH 9.6 for 16 hours at 4° C. The plates are rinsed with PBS containing 0.05% Tween 20 (PBS-T) and blocked with 200 µl of PBS containing 3% BSA (PBS-BSA) for 1 hour. The wells are rinsed 4 times with PBS-T and incubated with 100 µl of sample or standard Trx diluted in a serial manner in PBS-TB containing DTT (Dithiothreitol) 1 mM, over 2 hours at 4° C. The plates are covered with aluminium foil. The wells are rinsed 4 times with PBS-T and then incubated with 100 µl of biotinylated IgG of goat anti-human Trx (IMCO Co), 75 ng/ml, for 1 hour at ambient temperature on an orbital shaker.

The wells are then rinsed 4 times with PBS-T and incubated with 100 µl of streptavidin conjugated with alkaline phosphatase (AX02-0402X; 1:4000) (Amersham Biosciences) in PBS-BSA-T (0.1% BSA, 0.05% Tween 20) on an orbital shaker.

The plates are washed 4 times in PBS-T and incubated with p-nitrophenyl phosphate (Sigma Chem Co) in diethanolamine, pH 9.0, containing 0.5 mM $MgCl_2$, and 0.02% $NaN_3$ for 40 minutes.

The absorbance is measured at 405 nm.

The human recombinant Trx (IMCO Co) is used as a standard in the range 100-0.41 ng/ml.

The levels are expressed in ng of Trx/mg of total proteins present in the cell extract.

Results Under Normal Physiological Conditions (Donor Aged 15)

|  | Level (ng of TrxR/mg of total proteins) | % |
|---|---|---|
| Control | 87.6 ± 7.6 | |
| 0.5% of product A | 90.0 ± 4.2 | +3 |
| 1% of product A | 94.0 ± 4.7 | +7 |
| 2% of product A | 98.8 ± 10.2 | +13 |

|  | Level (ng of TrxR/mg of protein) | % |
|---|---|---|
| Control | 87.6 ± 7.6 | |
| 0.5% of product B | 88.4 ± 2.7 | +1 |
| 1% of product B | 95.7 ± 7.6 | +9 |
| 2% of product B | 99.8 ± 5.3 | +14 |

Results Under Normal Physiological Conditions (Donor Aged 15) in the Presence of N-Acetyl-cysteine (NAC), a Thioredoxin Inhibitor

|  | Level (ng of Trx/mg of total proteins) | % |
|---|---|---|
| Control | 87.6 ± 7.6 | |
| NAC (10 mM) | 59.8 ± 8.1 | −32 |
| NAC (10 mM) + 0.5% of product A | 60.2 ± 2.8 | +1 |
| NAC (10 mM) + 1% of product A | 61.4 ± 3.3 | +3 |
| NAC (10 mM) + 2% of product A | 63.1 ± 6.0 | +6 |
| Control | 87.6 ± 7.6 | |
| NAC (10 nM) | 59.8 ± 8.1 | −32 |
| NAC (10 mM) + 0.5% of product B | 60.4 ± 5.4 | +1 |
| NAC (10 mM) + 1% of product B | 61.0 ± 3.1 | +2 |
| NAC (10 mM) + 2% of product B | 65.4 ± 9.2 | +9 |

Results Under Physiological Senescence Conditions (Donor Aged 62)

|  | Level (ng of Trx/mg of total proteins) | % |
|---|---|---|
| Control | 61.6 ± 4.2 | |
| 0.5% of product A | 65.9 ± 6.0 | +7 |
| 1% of product A | 68.9 ± 2.6 | +12 |
| 2% of product A | 74.5 ± 4.2 | +21 |
| Control | 61.6 ± 4.2 | |
| 0.5% of product B | 66.9 ± 5.8 | +9 |
| 1% of product B | 70.4 ± 8.3 | +14 |
| 2% of product B | 77.3 ± 10.2 | +25 |

Results Under Photoinduced Senescence Conditions (Donor Aged 15, UVB 100 $mJ/cm^2$ of Culture)

|  | Level (ng of Trx/mg of total proteins) | % |
|---|---|---|
| Control | 87.6 ± 7.6 | |
| UVB | 93.4 ± 9.4 | +7 |
| UVB + 0.5% of product A | 95.8 ± 9.0 | +9 |
| UVB + 1% of product A | 100.7 ± 12.4 | +15 |
| UVB + 2% of product A | 109.1 ± 13.3 | +25 |
| Control | 87.6 ± 7.6 | |
| UVB | 93.4 ± 9.4 | +7 |
| UVB + 0.5% of product B | 94.8 ± 7.7 | +8 |
| UVB + 1% of product B | 106.5 ± 10.0 | +22 |
| UVB + 2% of product B | 114.1 ± 13.0 | +30 |

In the presence of product B, an increase is observed in the level of thiroredoxin greater than that obtained with product A alone.

EXAMPLE 9

Measurement of the Enzymatic Activities of the Phytoalexins Produced by the Cells Cultured Under the Stress Conditions According to Example 2

The activity of ferredoxin-NADP+ oxidoreductase (FNR) is determined by a calorimetric method based on the reduction of cytochrome c.

The reduction of cytochrome c, measured with a spectrophotometer at a wavelength of 550 nm, is directly proportional to the activity of the enzyme.

One unit of FNR reduces 1 millimole of cytochrome c per minute at pH 7.5, at 25° C. in the presence of ferrodoxin and NADPH.

The activity of the superoxide dismutase (SOD) is evaluated by its ability to inhibit a flow of superoxide anions generated by the xanthine-xanthine oxidase system. The superoxide radicals produced by this system reduce nitroblue tetrazolium (NBT) to stable blue formazan at 560 nm. An enzymatic unit of SOD corresponds to the quantity of vegetable extract capable of inducing a 50% inhibition in the reduction of the NBT.

Glutathione reductase regenerates reduced glutathione to glutathione which becomes available to the cell.

Results:

| Phytoalexin | Activity in units/ml of product, approximately: |
|---|---|
| SOD | 20 |
| CuZn SOD | 3.5 |
| Glutathione reductase | 0.5 |
| FNR | 2.5 |

FIG. 1 is a schematic representation of proteins processing in vivo. Damaged proteins are either eliminated by the proteosomal system or repaired, depending on the nature of the alteration.

FIG. 2 shows a measurement of the proteasome activity and more specifically of the proteasome subunits 20S, 26S and PA28, in keratinocyte cell cultures originating from a donor aged 15. The proteasome subunits 20S, 26S and PA28 are purified by immunoaffinity chromatography of cell culture extracts prepared from cells of a donor aged 15. The peptidase activity of each proteasome subunit is measured in the various chromatographic eluate fractions though the release of a fluorescent radical (MCA). FIG. 2 thus displays the measured fluorescence for each proteasome subunit (i.e. 20S, 26S and PA28) for each collected fraction.

FIG. 3 shows a measurement of the proteasome activity and more specifically of the proteasome subunits 20S, 26S and PA28, in keratinocyte cell cultures originating from a donor aged 62. The proteasome subunits 20S, 26S and PA28 are purified by immunoaffinity chromatography of cell culture extracts prepared from cells of a donor aged 62. The peptidase activity of each proteasome subunit is measured in the various chromatographic eluate fractions though the release of a fluorescent radical (MCA). FIG. 3 thus displays the measured fluorescence for each proteasome subunit (i.e. 20S, 26S and PA28) for each collected fraction.

FIG. 4 shows a measurement of the proteasome activity and more specifically of the proteasome subunits 20S, 26S and PA28, in keratinocyte cell cultures originating from a donor aged 15 and further submitted to photoinduced senescence conditions (UVB). The proteasome subunits 20S, 26S and PA28 are purified by immunoaffinity chromatography of cell culture extracts prepared from cells of a donor aged 15 and further submitted to photoinduced senescence conditions (UVB). The peptidase activity of each proteasome subunit is measured in the various chromatographic eluate fractions though the release of a fluorescent radical (MCA). FIG. 4 thus displays the measured fluorescence for each proteasome subunit (i.e. 20S, 26S and PA28) for each collected fraction.

The invention claimed is:

1. A cosmetic active ingredient consisting of arginine ferulate and of an extract of *Scenedesmus* microalgae, wherein the said *Scenedesmus* microalgae have been subjected to an oxidative stress treatment.

2. The active ingredient according to claim 1, wherein the arginine ferulate:extract of *Scenedesmus* microalgae ratio by weight ranges from 1:1 to 1:199.

3. The active ingredient according to claim 1, wherein the arginine ferulate:extract of *Scenedesmus* microalgae ratio by weight is 1:19.

4. An in vitro or ex vivo method of using the cosmetic active ingredient according to claim 1, for activating the proteasome of cells.

5. An in vitro or ex vivo method of using the cosmetic active ingredient according to claim 1, for stimulating the production of thioredoxin.

6. An in vitro or ex vivo method of using the cosmetic active ingredient according to claim 1, for the production of a cosmetic composition for topical use.

7. A cosmetic composition for topical use comprising the active ingredient according to claim 1 in a physiologically acceptable medium.

8. A method of using the cosmetic composition according to claim 7 for combating skin ageing.

9. The active ingredient according to claim 2, wherein the arginine ferulate:extract of *Scenedesmus* microalgae ratio by weight ranges from 1:19 to 1:99.

* * * * *